United States Patent [19]

Lacy et al.

[11] 4,389,904
[45] Jun. 28, 1983

[54] METHOD AND APPARATUS FOR SUPERCOOLING AND SOLIDIFYING SUBSTANCES

[75] Inventors: Lewis L. Lacy; Michael B. Robinson; Thomas J. Rathz; Lester Katz, all of Huntsville, Ala.; Daniel B. Nisen, Memphis, Tenn.

[73] Assignee: The United States of America as represented by the Administrator of the National Aeronautics and Space Administration, Washington, D.C.

[21] Appl. No.: 246,773

[22] Filed: Mar. 23, 1981

[51] Int. Cl.³ .......................................... G01N 25/04
[52] U.S. Cl. .................................. 73/863.11; 374/17
[58] Field of Search ............... 73/15 R, 17 R, 863.11; 264/5, 10; 374/16, 17, 121

[56] References Cited

U.S. PATENT DOCUMENTS

| | | | |
|---|---|---|---|
| 2,795,819 | 6/1957 | Lezberg et al. | 264/10 |
| 3,173,288 | 3/1965 | Davis et al. | 374/16 |
| 3,173,289 | 3/1965 | Davis | 374/16 |
| 3,496,760 | 2/1970 | Pozniak | 374/16 |
| 3,963,812 | 6/1976 | Schlienger | 264/10 |
| 4,313,745 | 2/1982 | Lovelace | 264/5 |

OTHER PUBLICATIONS

Lacy et al., "Containerless Undercooling and Solidification in Drop Tubes" in Journal of Crystal Growth, vol. 5, 1981, pp. 47-60.

*Primary Examiner*—Herbert Goldstein
*Attorney, Agent, or Firm*—J. H. Beumer; J. R. Manning; L. D. Wofford, Jr.

[57] ABSTRACT

A method and apparatus for preparing and studying samples of materials supercooled and solidified in a containerless, low-gravity environment in bulk form is disclosed which includes an enclosure 10 in which a containerless environment is provided in which a sample specimen 52 is positioned. Method contemplates heating the specimen 52 in the containerless environment, dropping the specimen melt through the tube 12 wherein it cools by radiation, and alternately backfilling the tube 12 with an inert gas whereby the specimen melt cools by both radiation and convection during its free fall. During the free fall, the sample is in a containerless, low-gravity environment which will enhance supercooling in the sample and prevent sedimentation and thermal convection influences. The sample will continue to supercool until nucleation occurs which is detected by silicon photovoltaic detectors. The sample will solidify after nucleation and be completely solid before entering the detachable catcher. The amount of supercooling of the specimen can be measured by knowing the cooling ratio and determining the time for nucleation to occur.

9 Claims, 3 Drawing Figures

METHOD AND APPARATUS FOR SUPERCOOLING AND SOLIDIFYING SUBSTANCES

ORIGIN OF THE INVENTION

The invention described herein was made by employees of the U.S. Government and may be manufactured and used by or for the Government for governmental purposes without the payment of any royalties thereon or therefor.

BACKGROUND OF THE INVENTION

In the last decade, there has been an increased interest in the use of orbital space environment to carry out experiments associated with low-gravity solidification processes.

In a low-gravity environment, the levitation of large samples can be achieved by using only small forces to overcome residual spacecraft motion. One can easily levitate and independently heat materials to elevated temperatures using only modest amounts of heating power. Materials can be prepared and studied without introducing crucible effects. Supercooling becomes a natural extension in such an environment since the elimination of crucibles allows ease of superheating to dissolve heterogeneous nucleants and the elimination of container-induced nucleation. Thus, the space environment can allow for large supercooling in "bulk" form for various high-temperature metals, alloys or glasses.

The supercooling of liquid metals and alloys below their equilibrium melting temperature has been widely studied. In normal container casting techniques, only modest supercooling of a few degrees takes place since catalytic sites usually initiate nucleation and crystal growth. Catalysis for heterogeneous nucleation includes contact with crucible walls and various undissolved dispersents within the melt. In order to supercool a liquid metal to the maximum extent, various techniques have been developed to remove container nucleation effects and to eliminate heterogeneous nucleants from the melt. One technique generally known as the emulsion technique involves breaking the metal up into small droplets (diameter 2-10 $\mu m$) and dispersing the droplets in a carrier fluid or placing the droplets on clean substrates. The emulsion technique helps eliminate both types of nucleation provided that the droplets are covered by an inert film consisting of an oxide, sulfide or salt. The droplet technique allows major supercooling because it disperses the heterogeneous nucleants to only a few of the drops and thereby frees the remaining drops to supercool to some lower nucleation temperature.

In addition to the previously discussed techniques, another technique developed to provide for containerless supercooling and solidification of small molten drops is commonly known as the droplet technique. Small molten drops of refractory metals are formed by utilizing the discharge of a capacitor or a pulsed laser into fine wires of the sample such as Nb and Ta. The wires melt very rapidly and form small droplets. The droplets are thrown in various directions and at various velocities by the force of the exploding wire. The droplets are solidified as small spheres and supercooling may be provided by cooling in a gaseous or liquid helium environment. The amount of supercooling achieved was believed to be in the range of several hundred Kelvin. This technique provided spherical single crystals of metals with diameters in the range of 0.1 to 0.5 mm. The exploding-wire technique has several disadvantages. This technique is limited to samples in wire form only, which eliminates the processing of glasses and brittle alloys. Also the samples produced are extremely small, in the range of 0.1 to 0.5 mm. Due to the method of heating, this techniques offers very little or no control over heating, melting, and solidification of the samples.

Another technique for studying containerless supercooling in bulk form involves the use of electromagnetic (EM) levitators which operate by passing a high frequency oscillating current through a precisely formed coil. A field is set up in the coil which can levitate and heat a sample. The sample can be heated, melted, cooled, and resolididified by control of the coil current and a flowing cooling gas. Electromagnetic levitators suffer from the disadvantage of a low coupling efficiency which depends upon sample size and shape. This technique also develops large thermal gradients within the sample which result in severe convection currents. The severe convection current results in the loss of low vapor pressure phases within alloy samples and also leads to smaller amounts of supercooling due to possible dynamic nucleation effects and the introduction of surface oxides into the sample interior. Another disadvantage of levitation is the limitation to independently control sample levitation size and temperature, particularly for higher melting point materials. Likewise, EM levitation cannot simulate low-gravity conditions and, thus, they cannot suppress phase separation processes such as sedimentation and solutal convection. Both techniques also are limited to electrically conducting samples.

While several of the above developments and studies have identified the beneficial reasons for using a containerless environment in achieving major supercooling, a direct quantitative comparison between using containerless techniques and in using dispersion or droplet techniques cannot usually be made. The reason for this is that accurate supercooling data is usually not available for freely falling molten particles.

Zero gravity enrivonments have been provided for other purposes such as calibrating instrumentation used in outer space as shown in U.S. Pat. No. 3,408,870.

Accordingly, an important object of the present invention is to provide apparatus to supercool and solidify pure materials and alloys in a containerless, low gravity environment.

Another important object of the present invention is to make certain metastable alloys and compounds in bulk form which have heretofore been unable to be made in such form.

Still another important object of the present invention is to provide apparatus for economically producing spherical single crystals of pure metals and alloys.

Still another object of the invention is to provide an apparatus to produce droplets of oxide glasses or amorphous alloys.

SUMMARY OF THE INVENTION

It has been found that a method and apparatus for containerless low-gravity environment can be had to supercool and solidify metals, alloys or glasses which eliminate crucible-induced nucleation processes by providing a furnace and drop tube assembly constructed to study low-gravity solidification of containerless melts. Niobium (Nb) droplets with diameters in the range of 2 to 5 mm have been supercooled by 525 K which exceeds the maximum supercooling achieved on small, low-melting temperature droplets. Solidification at such large supercooling results in single crystalline spheres with the formation of interdendritic shrinkage channels on the sample surface rather than interior shrinkage cavities. The grain refinement observed for nickel samples supercooled and solidified in fused silica crucibles does not occur. The reason for single crystal growth in supercooled Nb is believed to be associated with the large supercooling and containerless solidification in a low-gravity environment. A solidification speed of 320 m/s has been found for the Nb drops. This solidification speed is greater than or comparable to the solidification speeds calculated in splat cooled samples. The furnace drop tube apparatus can be useful in the preparation and study of high temperature metastable compounds or alloys in bulk form. The drop tube apparatus has also been used to supercool and cast amorphous alloys, such as Pd-Si-Cu with diameters in the range of 0.5 to 2.0 mm.

BRIEF DESCRIPTION OF THE DRAWING

The construction designed to carry out the invention will be hereinafter described, together with other features thereof.

The invention will be more readily understood from a reading of the following specification and by reference to the accompanying drawing(s) forming a part htereof, wherein an example of the invention is shown and wherein:

FIG. 1a is a partial schematic diagram of a suitable heating technique for use with the present invention.

DESCRIPTION OF A PREFERRED EMBODIMENT

The invention relates to apparatus and method for studying and analyzing supercooling phenomena of various high temperature metals and alloys in a low-gravity, containerless environment, and, more particularly, to a furnace and drop tube apparatus having an economical construction and operation which allows numerous material samples to be prepared with various parameters and with a low cost per sample ratio. Flexibility to change parameters is provided during the experiment along with a short turnaround time to capitalize on unexpected results occurring during experimentation.

Figure 1:
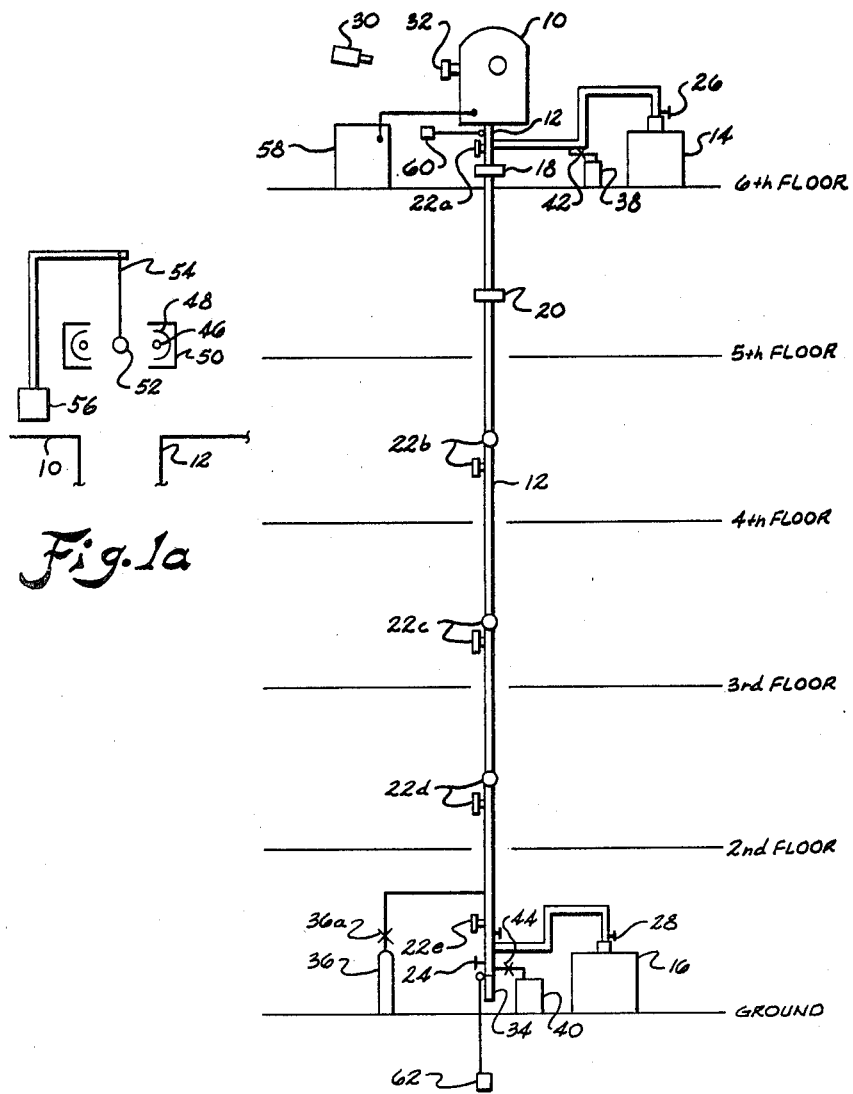
FIG. 1 is a schematic illustration of a method and apparatus for containerless supercooling and solidification of substances.

Referring now to the drawings, a schematic illustration of a furnace and drop tube apparatus is illustrated in FIG. 1 which may be employed to carry out the invention. Containerless enclosure means for a furnace and a sample specimen is provided by a stainless steel bell jar housing 10 which is positioned directly over and in open communication with a stainless steel drop tube 12. In one embodiment, a tube 12 was utilized having a 10 centimeter inside diameter and a length of approximately 100 ft. The furnace contained within the bell jar housing 10 may be any suitable sample melting apparatus appropriate for the material being processed and which will form molten drops of the sample such as disclosed in U.S. Pat. No. 4,248,083 issued on Feb. 3, 1981, wherein the sample material is suspended from a fine wire and heated by electron bombardment. Other furnace designs using radiant heating zones and ellipsoidally focused lamps have also been found suitable for processing samples with melting temperatures up to 1600° C.

The bell jar housing enclosure 10 and drop tube assembly 12 are evacuated by vacuum source means which includes upper turbomolecular pump 14 which preferably evacuates the system to a pressure of $1 \times 10^{-5}$ Torr. A second lower turbomolecular pump 16 may be provided and connected adjacent the bottom of drop tube 12 as required by the length of the drop tube to properly evacuate the entire assembly uniformly. Conventional electropneumatically-operated valves 18 and 20 are connected to the drop tube at various sections to provide means for isolating the drop tube and bell jar and different drop tube sections for reasons which will become apparent. For example, during the placement of a specimen sample in the housing enclosure, valve 18 may be closed to maintain the vacuum in drop tube 12. When closed, valves 18 and 20 close communication between adjacent environments; and, when open, allow open communication and the unobstructed dropping of the sample specimen from enclosure 10 through drop tube 12. Electropneumatic valves 18 and 20 may be any suitable vacuum valves which are operated pneumatically in response to an electrical signal such that they may be controlled remotely for convenience. Suitable valves are available from Airco Temescal Co., model no. 5130-x, 4 inch valves. Hand-operated isolator valve 24 is a conventional beveled vacuum valve which may be closed to maintain the vacuum conditions within the drop tube during retrieval of a sample. Upper and lower vacuum pumps 14 and 16 may be isolated and cut off from the system by means of manual isolator valves 26 and 28 which may be any suitable on-off vacuum valves, as valve 24. Various instrumentation and viewing ports 22a-22e are located on each floor level, ground through 6th floor level through which the sample may be viewed during heating and melting. During the heating and melting process, the temperature of the sample may be monitored by an optical pyrometer 30 by direct viewing through pyrometer view port 32.

A detachable sample catcher 34 is mounted onto the bottom of the drop tube assembly 12, which deaccelerates and catches the sample. During free fall, the sample will be cooled either by radiation or by both radiation and convection. In the case of convection, the drop tube may be backfilled with an inert gas, supplied by an inert gas supply 36 which is preferably a helium gas. In one example, radiation cooling was found sufficient for niobium samples of up to five millimeter (mm.) in diameter. These samples were deaccelerated and caught by using a sample catcher 34 whose inner surface was lined with niobium foils. While free falling, the sample is in a containerless, low gravity environment which will enhance supercooling in the sample and prevent sedimentation and thermal or solutal convection. The sample will continue to supercool until nucleation occurs at which time the sample will solidify and, therefore, be completely solid for entering the detachable catcher.

Roughing pumps 38 and 40 may be provided along with the turbomolecular pumps 14 and 16 to achieve partial vacuum conditions before using the turbomolecular pumps. These vacuum pumps can be isolated from the rest of the system by closing the vacuum valves 26, 28, and 42, 44 when operating with the inert gas environment. If desired, a sample can be melted in a vacuum environment and allowed to fall through an inert gas by closing the electropneumatic vacuum valves 18 and 20 and backfilling the section below the electropneumatic valves with an inert gas while evacuating the bell jar with the upper turbomolecular pump 14. When the sample is released, the electropneumatic valves are opened allowing the sample to fall through the lower section of the tube filled with an inert gas. The sample catcher is detached and the sample is removed. After the specimen catcher 36 is detached and replaced, this section of the drop tube assembly can be evacuated by the lower roughing pump 40 before the catcher isolator valve 24 is reopened.

A suitable containerless melting apparatus has been referred to heretofor which is based upon the pendant drop technique using omnidirectional electron bombardment. The previously referred to patent may be referred to for more detail. The bombarding electrons are supplied by a hot circular cathode 46 which is maintained at a high negative potential. The focusing grid 48, which is torroidal in shape, is maintained at the same negative potential as the cathode and helps concentrate the electrons onto the sample surface. A cylindrical equipotential grid helps prevent electron loss to the bell jar enclosure 10 and prevents heating to the support wire. The sample 52 is maintained at the ground potential and is suspended from a support wire 54 made out of the major constitutent element (i.e., Nb for Nb alloys). The sample can be raised or lowered into the heating apparatus by means of a gear box 56 which is controlled from outside the bell jar using a magnetic-coupled feedthrough. The emission current striking the sample is accurately measured by electrically isolating the support assembly and letting the current flow to the ground potential through an isolated ammeter circuit. The current striking the sample, and consequently the heating power, can be accurately controlled by using a ten-turn pot located on the power supply 58 or by the position of the sample in the melting apparatus. The brightness temperature of the sample can be continuously monitored and digitally recorded by an automatic fast response pyrometer at 30. The true thermal history of the sample during the heating and melting operation is determined once the spectral emissivity of the sample is measured by a conventional technique not discussed here.

The design of the melting apparatus provides for isothermal heating of the sample with no more than 25 K gradients across a 5 mm sample at 2750 K. The heating efficiency is high since pure Nb samples have been melted (melting point 2741 K) with only 30 watts of power and Nb alloys with melting temperatures at 2300 K with only 15 watts. Other samples that have been successively melted include W (3683 K), Ta (3269 K), V (2173 K), Pt (2042 K), and Cu (1356 K). The sample shape is not critical and can be in the form of wires, small rods or a disk. The mass of the sample in controlled by surface tension of the liquid and the diameter of the wire. The mass of the sample is usually adjusted to within a few milligrams of the critical mass. If the sample mass is below the critical value, alloy samples can usually be superheated by several hundred degrees depending upon the melting temperature of the sample and support wire. If the support wire and sample consist of the same pure material, superheating will typically be less than 40 K. Consequently, if such a sample is below the critical value, the wire adjacent to the drop will melt and increase the drop mass until it finally reaches its critical value.

When the surface tension of the drop can no longer support the mass of the sample, the sample will fall into tube assembly 12 and begin supercooling. The supercooling of the drop will continue until nucleation takes place which will result in rapid crystal growth and solidification of the sample with a subsequent rapid rise in the temperature of the drop due to the release of the latent heat of fusion. Thus recalescence appears as a sudden flash of light over the normal radiation emitted by the drop at the nucleation temperature. This increased luminosity of the sample can be measured by detectors sensitive to the near infrared region (i.e., 0.7 to 2 $\mu$m). A 4% change in detector output would correspond to a 1% change in the sample temperature. Consequently, for samples with temperatures (T) near 2200 K any recalescence for T in excess of 22 K (i.e., 1% of 2200) should be easily detected on a fast response recorder as a 4% or greater change in the luminosity of the sample.

In practice, detector means for detecting luminosity of the sample is provided by two conventional silicon photovoltaic detectors installed in the system. These detectors have a spectral response of 0.53 to 1.06 $\mu$m (full width at half maximum) and are good for detecting black body radiation for temperatures in the range of 1500 K to 3500 K. One Si detector, illustrated schematically at 60, is at the top of the tube looking down with an acceptance angle of 0.7° and the other Si detector, illustrated schematically at 62, is at the bottom of the tube looking up with an acceptance angle of 7.5°. This arrangement is more than adequate to detect the luminosity of the falling drops at any location in the tube except for the first 20 cm of free fall. Suitable detectors are manufactured by United Detector Technology, Inc., Culver City, Ca., as model no. UDT-450D.

Figure 2:
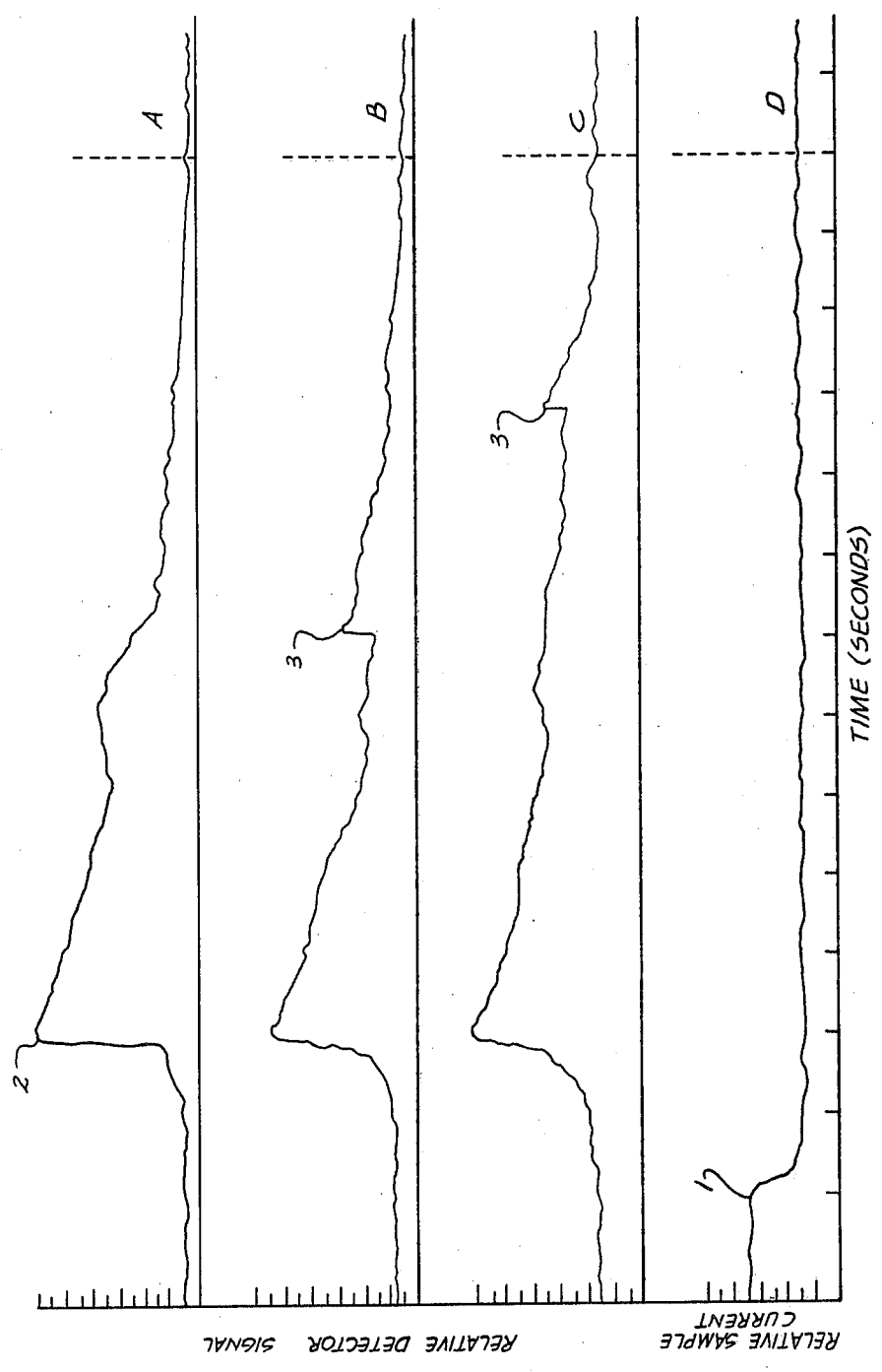
FIG. 2 is a graphic illustration which illustrates the current in a test specimen during heating and the luminosity during solidification of a falling drop as a function of time.

FIG. 2 shows three separate strip chart traces for the top Si detector voltages expressed in relative units (Curves A, B, C) and a typical trace (Curve D) for the heating current striking the sample before release. Curve D at point 1 can be used to determine the precise time the drop is released into the tube. Curve A is the detector output for a molten Nb sample which did not supercool since it contained some solid Nb upon release. Curves B and C are traces for two molten Nb samples which supercooled in a vacuum, each by 530 K. Curve B is for a smaller sample (D=3 mm) than Curve C (D=5 mm). The common peak identified as point 2 in all curves corresponds to the points in time (i.e.=0.4 s) when the molten sample comes directly into the field of view of the detector. Previous to Point 2, the detector picked up some light emitted by the sample and reflected from the bell jar into the tube. Nucleation and recalescence corresponds to a sudden increase in the brightness temperature of the sample at point 3 and is distinguishable from stray reflections by the rapid rise time. Although the samples in Curves B and C supercool by the same amount, the nucleation time corresonding to point 3 is quite different due to the different cooling rates, which is diameter dependent for the two samples. Thus, by independently determining the cooling rate and the nucleation time, an accurate determination of the supercooling can be made in accordance with conventional techniques. A more detailed description can be found in Lacy, et al., *Containerless Undercooling and Solidification in Drop Tubes*, 51 Journal of Crystal Growth, p. 47-60 (1981).

While a preferred embodiment of the invention has been described using specific terms, such description is for illustrative purposes only, and it is to be understood that changes and variations may be made without departing from the spirit or scope of the following claims.

What is claimed is:

1. A method of preparing and studying supercooled and solidified samples of materials in bulk form in a low gravity environment comprising:

providing an enclosure;

positioning a sample specimen of said material in an environment out of contact with said enclosure;

heating said specimen to form a specimen melt;

providing a drop tube assembly having a hollow drop tube disposed at a level generally below said specimen positioned in alignment therewith having a sufficient height to facilitate supercooling of said specimen melt falling therethrough;

supercooling said specimen melt by allowing said melt to fall freely through said drop tube wherein said melt is cooled by radiation and solidifed; and catching said solidified specimen adjacent the end of drop tube whereby said specimen may be removed for analysis.

2. The method of claim 1 including detecting the nucleation point of said specimen melt during its fall through said drop tube and measuring the amount of supercooling.

3. The method of claim 1 including isolating said enclosure and said drop tube assembly prior to heating said specimen, filling said drop tube with an inert gas, deisolating said enclosure and drop tube assembly after heating and before said specimen falls freely whereby said specimen melt is cooled both by radiaton and convection during its free fall.

4. The method of claim 1 including evacuating said enclosure and drop tube assembly prior to heating said specimen.

5. The method of claim 1 including providing a specimen catcher device detachably carried adjacent the bottom of said drop tube for catching said specimen.

6. The method of claim 5 including:

isolating said drop tube from said catcher device prior to detaching said device for removing said specimen;

reattaching said catcher device to said drop tube;

evacuating said catcher device; and deisolating said drop tube and catcher device following reattachment of said device whereby a uniform vacuum is established therein.

7. Apparatus for preparing and studying supercooled and solidified samples of material in low gravity environment generally out of contact with any container comprising:

enclosure means providing an enclosed environment in which a sample specimen of said material may be positioned out of contact with said enclosure;

a drop tube assembly having a drop tube carried generally below the level of said enclosure means in substantial alignment with said specimen positioned thereon;

vacuum means including a first vacuum source evacuating said enclosure means and drop tube;

valve means for selectively connecting and disconnecting open communication between said enclosure means and drop tube for maintaining vacuum conditions independently therewith while being opened to allow free fall of said specimen through said drop tube;

a detachable catcher member included in said drop tube assembly removably carried adjacent an end of said drop tube for catching said specimen;

said vacuum means including a second vacuum source for evacuating said catcher member independently from said enclosure means and drop tube; and an isolator valve for selectively isolating said catcher member from said drop tube allowing removal of said catcher member and specimen without effecting the environment of said drop tube and enclosure means;

whereby a specimen heated and melted in said enclosure means is supercooled and solidified during free fall in said drop tube and removed subsequently from said catcher member.

8. The apparatus of claim 7 wherein said vacuum means includes upper and lower vacuum means communicating respectively with said enclosure means and a lower portion of said drop tube for uniformly evacuating said enclosure means and drop tube.

9. The apparatus of claim 7 including a source of inert gas means in fluid communication with said drop tube, and valve means connected between said gas source and drop tube for connecting and disconnecting said communication.

* * * * *